United States Patent
Kramer et al.

(10) Patent No.: US 9,920,337 B2
(45) Date of Patent: Mar. 20, 2018

(54) METHODS FOR PRODUCING CARBON-BASED CHEMICALS BY ALGAL BIOMASS PROCESSING

(71) Applicant: DIREVO Industrial Biotechnology GmbH, Cologne (DE)

(72) Inventors: Marco Kramer, Cologne (DE); Klaudija Milos, Cologne (DE)

(73) Assignee: DIREVO Industrial Biotechnology GmbH, Cologne (DE)

(*) Notice: Subject to any disclaimer, the term of this patent is extended or adjusted under 35 U.S.C. 154(b) by 0 days.

(21) Appl. No.: 14/904,470

(22) PCT Filed: May 20, 2014

(86) PCT No.: PCT/EP2014/060302
§ 371 (c)(1),
(2) Date: Jan. 12, 2016

(87) PCT Pub. No.: WO2015/007419
PCT Pub. Date: Jan. 22, 2015

(65) Prior Publication Data
US 2016/0355848 A1     Dec. 8, 2016

Related U.S. Application Data

(60) Provisional application No. 61/846,304, filed on Jul. 15, 2013.

(30) Foreign Application Priority Data

Jul. 15, 2013    (EP) ..................................... 13176443

(51) Int. Cl.
C12P 7/56      (2006.01)
C12P 7/06      (2006.01)

(52) U.S. Cl.
CPC .................. *C12P 7/56* (2013.01); *C12P 7/065* (2013.01); *Y02E 50/17* (2013.01)

(58) Field of Classification Search
None
See application file for complete search history.

(56) References Cited

U.S. PATENT DOCUMENTS

2016/0355848 A1* 12/2016 Kramer .................. C12P 7/065

FOREIGN PATENT DOCUMENTS

| EP | 2740799 A2 | 6/2014 |
| WO | 2010/035142 A2 | 4/2010 |
| WO | 2013/041668 A1 | 3/2013 |
| WO | 2013/050583 A1 | 4/2013 |

OTHER PUBLICATIONS

Kadar et al. (Appl. Biochem. & Biotech., vol. 113-116, 2004, p. 497-508).*
Talukder et al. (Biochem. Engin. J., vol. 68, 2012, pp. 109-113).*
PCT/EP2014/060302 International Search Report dated Sep. 26, 2014.
Efremenko et al. "Production of biofuels from pretreated microalgae biomass by anaerobic fermentation with immobilized Clostridium Acetobutylicum cells." Bioresource Technology, Mar. 2012, 114(16):342-348, Elsevier BV, GB.
Kanno and Toriyama. "Production of Ethanol by a Thermophilic Anaerobic Bacterium and Its Ethanol-Tolerant Mutant." Agricultural and Biological Chemistry, Jan. 1, 1986, 50(1):217-218.
Talukder et al. "Microalgae (Nannochloropsis salina) biomass to lactic acid and lipid." Biochemical Engineering Journal, Oct. 1, 2012, 68:109-113.

* cited by examiner

*Primary Examiner* — Hope Robinson
(74) *Attorney, Agent, or Firm* — Wagenknecht IP Law Group PC

(57) ABSTRACT

The present technology relates to novel methods for converting algal biomass material for the production of carbon-based chemicals, in particular carboxylic acids like lactic acid using extremely thermophilic microorganisms.

8 Claims, No Drawings

METHODS FOR PRODUCING CARBON-BASED CHEMICALS BY ALGAL BIOMASS PROCESSING

CROSS-REFERENCE TO RELATED APPLICATIONS

This application is a U.S. National stage of PCT/EP2014/060302 filed May 20, 2014, which claims priority to EP Application Serial No. 13176443.3 filed Jul. 15, 2013 and U.S. Provisional Application Ser. No. 61/846,304 filed Jul. 15, 2013, each of which is incorporated herein by reference in its entirety.

FIELD OF THE INVENTION

The present disclosure relates to novel methods for converting algal biomass material for the production of carbon based chemicals, in particular carboxylic acids like lactic acid using extremely thermophilic microorganisms.

BACKGROUND OF THE INVENTION

In general, fermentation products are produced by degradation of starch-containing material into fermentable sugars by liquefaction and saccharification followed by conversion of the sugars directly or indirectly into the desired fermentation product using a fermenting organism.

For example, many carboxylic acids are produced industrially on a large scale. They are also pervasive in nature. Carboxylic acids are used in the production of polymers, pharmaceuticals, solvents, and food additives. Industrially important carboxylic acids include acetic acid (component of vinegar, precursor to solvents and coatings), acrylic and methacrylic acids (precursors to polymers, adhesives), adipic acid (polymers), citric acid (beverages), ethylenediaminetetraacetic acid (chelating agent), fatty acids (coatings), maleic acid (polymers), propionic acid (food preservative), terephthalic acid (polymers). Lactic acid is widely used in food, pharmaceutical and textile industries. It is also used as a source of lactic acid polymers which are being used as biodegradable plastics. The physical properties and stability of polylactides can be controlled by adjusting the proportions of the L(+)- and D(−)-lactides. Optically pure lactic acid is currently produced by the fermentation of glucose derived from corn starch using various lactic bacteria (Kenji Okano, Qiao Zhang, Satoru Shinkawa, Shogo Yoshida, Tsutomu Tanaka, Hideki Fukuda, and Akihiko Kondo (2009). Efficient production of optically pure D-lactic acid from raw corn starch by using a genetically modified L-lactate dehydrogenase gene-deficient and -amylase-secreting *Lactobacillus plantarum* strain. Applied and Environmental Microbiology, 75, 462-467).

However, the lactic bacteria have complex nutritional requirements and the use of corn as the feedstock competes directly with the food and feed.

Feedstocks not competing directly with food and feed are naturally resistant lignocellulosic biomass. Lignocellulose is the non edible part of plants. Using lignocellulose to produce carboxylic acid avoids competition with the food industry. Lignocellulose is the most abundant renewable biomass. The yield of lignocellulose can reach approximately 200 billion metric tons worldwide per year (Zhang, Y. H. P., S. Y. Ding, J. R. Mielenz, J. B. Cui, R. T. Elander, M. Laser, M. E. Himmel, J. R. McMillan, and L. R. Lynd. (2007). Fractioning Recalcitrant Lignocellulose at Modest Reaction Condition. Biotechnology and Bioengineering. 97(2): 214-23). Lignocellulose is a feedstock with a low production cost. Lignocellulose can be found everywhere and is available as waste biomass, including agricultural residues (wheat straw, sugarcane bagasse, and corn stover), energy crops (switch grass), and municipal solid waste (paper and paperboard products) (Hamelinck, C. N., V. H. Geertje, and A. P. C. Faaij. (2005). Ethanol from Lignocellulosic Biomass: Techno-Economic Performance in Short-, Middle- and Long-Term." Biomass and Bioenergy 28(4):384-410.).

However, the characteristics of lignocellulose have different disadvantages for the usage as feedstock not competing with food and feed. Because lignocellulose is mainly made up of lignin, hemicellulose, and cellulose fibers this combines to form a firm, very compact network structure. In a natural state, after size reduction, the access to cellulose is still blocked by lignin and hemicellulose because of the intact cell wall structure. Moreover, cellulose has a highly crystalline structure that is very difficult to break down (Hsu, T. A., M. Ladisch, and G. Tsao. (1980). Alcohol from Cellulose. Chem. Technol. 10(5):315-19.). Therefore harsh pre treatment processes are currently used to destroy the structure of lignocellulosic biomass plant cell walls and make cellulose more accessible to the subsequent process of hydrolysis (during hydrolysis, cellulose is broken down into simple sugars).

Pre treatment methods can be categorized into four types: physical methods (e.g., milling and grinding); physico-chemical methods (e.g., steam explosion or hydrothermolysis); chemical methods (e.g., using acids, alkali, oxidizing agents, or organic solvents to treat biomass); and biological methods (e.g., using microorganisms and fungi to treat biomass) (Kumar, P., D. M. Barrett, M. J. Delwiche, and P. Stroeve. (2009). Methods for Pretreatment of Lignocellulosic Biomass for Efficient Hydrolysis and Biofuel Production. Industrial & Engineering Chemistry Research 48(8): 3713-29.). However, only those pre treatment methods that employ chemicals currently offer the high yields and low costs vital to economic success. Among the most promising are pre treatments using dilute acid, sulfur dioxide, near-neutral pH control, ammonia expansion, aqueous ammonia, and lime, with significant differences among the sugar-release patterns.

Although pre treatment of naturally resistant cellulosic materials is essential, if high yields from biological operations should be achieved; this operation is projected to be the single, most expensive processing step. For example about 20% of the total cost for the production of ethanol are based on the pre treatment process (Bin Yang and Charles E. Wyman. (2008). Pre treatment: the key to unlocking low-cost cellulosic ethanol. Biofuels, Bioprod. Bioref. 2:26-40). Moreover, pretreatment of lignocellulosic biomass will generally release extractives and other natural products and can form degradation products, such as lignin fragments and derivatives thereof, which are inhibitory or even toxic to downstream enzymes and organisms (Bin Yang and Charles E. Wyman. (2008). Pre treatment: the key to unlocking low-cost cellulosic ethanol. Biofuels, Bioprod. Bioref. 2:26-40). This will reduce the productivity of any subsequent fermentation process with pretreated lignocellulosic biomass as feed stock, if approaches to circumvent this are not used.

Therefore, the availability and use of novel feedstocks for the production of carbon-based chemicals like carboxylic acids would be highly advantageous.

SUMMARY OF THE DISCLOSURE

The present disclosure relates to methods using extreme thermophilic microorganisms for converting algal biomass to carbon based chemicals like carboxylic acids, in particular lactic acid and/or acetic acid.

In a first aspect, embodiments of the disclosure provide methods for converting an algal biomass to a carbon-based chemical, comprising the steps of contacting the algal biomass with a microbial culture for a period of time at an initial temperature and an initial pH, thereby producing an amount of the carbon-based chemical.

In still another aspect the present disclosure relates to methods of producing lactic acid from algal biomass material converting the algal biomass material to lactic acid in a single step process, the method comprising:
a) Culturing and growing algae in a liquid medium to a desired algae biomass,
b) Combining a microbial culture and the algal biomass; and
c) Fermenting the algal biomass under conditions and for a period of time sufficient to produce lactic acid, a salt or a ester thereof, and optionally
d) isolating said lactic acid, a salt or a ester thereof.

Embodiments of this disclosure relate to the use of microorganisms of the genus *Caldicellulosiruptor* and/or microorganisms of the genus *Thermoanaerobacter* for in the before mentioned methods.

In still another aspect, embodiments of this disclosure relate to methods for converting algal biomass material to a carboxylic acid, in particular lactic acid and/or acetic acid comprising the step of contacting the algal biomass material with a microbial culture for a period of time at an initial temperature and an initial pH, thereby producing an amount of a carboxylic acid, in particular to lactic acid, wherein the microbial culture comprises an extremely thermophilic microorganism, in particular a microorganism of the genus *Caldicellulosiruptor*, in particular a microorganisms listed in Table 1 or Table 2, microorganisms derived from either of these strains or mutants or homologues thereof.

Before the disclosure is described in detail, it is to be understood that this disclosure is not limited to the particular process steps of the methods described herein. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

To provide a comprehensive disclosure without unduly lengthening the specification, the applicant hereby incorporates by reference each of the patents and patent applications cited herein.

DESCRIPTION OF THE DISCLOSURE

The present disclosure relates to methods using extreme thermophilic microorganisms for processing algal biomass to carbon-based chemicals like lactic acids or derivatives thereof. The disclosure relates, in certain aspects, to the use of thermophilic microorganisms, which are able to convert algal biomass such as, for example, the micro alga *Nannochloropsis salina*, to soluble products that can be used by the same or by another microorganism to produce an economically desirable product such as carboxylic acids, in particular to lactic acid and/or acetic acid, salts or esters thereof.

The application of this technology has the potential to render production of carboxylic acids more economically feasible and to allow a broader range of microorganisms to utilize recalcitrant biomass. The use of cellulosic materials as sources of bioenergy is currently limited by typically requiring preprocessing of the cellulosic material. Such preprocessing methods can be expensive. Thus, methods that reduce dependence on preprocessing of cellulosic materials may have a dramatic impact on the economics of the use of recalcitrant biomass for biofuels production. One challenge in converting biomass into fermentation products is the recalcitrance and heterogeneity of the biological material. The present inventors have found microorganisms of the genus *Caldicellulosiruptor*, which have a variety of advantageous properties for their use in the conversion of algal biomass material to carboxylic acids, preferably in a single step process.

Algal biomass represents a potentially inexpensive and renewable source of sugars for fermentation. Therefore, the industry of producing fermentation products such as lactic acid is facing the challenge of redirecting the production process from fermentation of relatively easily convertible but expensive starchy materials, to the inexpensive algal biomass.

The algae represent a diverse group of primitive photosynthetic eukaryotes that inhabit most littoral freshwater, marine and terrestrial ecosystems of the planet. The diverse morphology forms exhibited by algae include microscopic unicells, colonies, filaments and large and complex thalli (i.e. three-dimensional 'bodies' like seaweeds). Recent molecular evidence reveals that organisms called 'algae' fit into very different evolutionary lineages including those related to plants, fungi or animals (Lucentinii J (2005) Secondary endosymbiosis exposed. The Scientist 19: 22-23).

Unlike starch, which contains homogenous and easily hydrolyzed polymers, algal biomass contains algal cell walls, which often represent the dominant component of the extracellular matrix and represent the largest or a significant percentage of the photosynthetically fixed carbon of the algae. Walls are typically fibrous composites of microfibrillar polysaccharides embedded in matrix polysaccharides and proteoglycans (reviewed by Domozych, David S (September 2011) Algal Cell Walls. In: eLS. John Wiley & Sons, Ltd: Chichester. DOI: 10.1002/9780470015902.a0000315.pub3). The diverse array of cell walls exhibited in the various algal groups is a manifestation of ancient evolutionary origins and ecological pressures of modern earth habitats.

As opposed to higher plants from example those comprising the group of Tracheophyta the presence of lignocellulose in the cell wall of algae is quite rare or absent (Patrick T. Martonel, José M. Estevez, Fachuang Lu, Katia Ruel, Mark W. Denny, Chris Somerville, John Ralph: Discovery of Lignin in Seaweed Reveals Convergent Evolution of Cell-Wall Architecture. Current Biology 19 (2), 27. January 2009; S. 169-175). Therefore the harsh pre treatment processes required for treating lignocellulosic biomass plant cell walls can be reduced or abolished by using algae biomass as feedstock. This makes the use of algal biomass as a lignocellulose depleted feedstock very advantages, since production of inhibitory or even toxic compounds from a pre treatment process will be reduced or abolished and moreover will reduce the costs. Additionally, algae are produced in closed photoreactors or ponds they will not compete directly with the food and feed, which are produced on agricultural land.

The use of extremely thermophilic microorganisms in fermentation processes with algal biomass has several advantages: High temperatures can weaken the cell walls of algae more easily than low temperatures making algal biomass better degradable for hydrolyzing microorganisms. This will decline the length of fermentation processes and therefore will reduce the costs of fermentation processes, since more fermentations can be performed in the same time period. Moreover, fermentation processes with thermophilic organisms this can be carried out in only one fermentation reactor simplifying the process compared to mesophilic or psychrophilic organisms. A further advantage is the possibility to do the conversion of the algal biomass to the carbon-based chemical without a pretreatment of the algal biomass.

The green algae (Chlorophyta) as an example represent the ancestral lineage of land plants and comprise a large and diverse group of organisms. Like higher plants, these algae possess chlorophylls a and b, double membrane-bound chloroplasts and, in most cases, starch as the main food reserve.

The lineage, Chlorophyta, contains an assortment of unicellular to multicellular, motile to nonmotile forms. The best-studied members within this class are the volvocalean *flagellates* (Volvocales) represented by such distinct genera as the unicellular *Chlamydomonas*, and the colonial Volvox (Voigt J and Frank R (2003) 14-3-3 proteins are constituents of the insoluble glycoprotein framework of the *Chlamydomonas* cell wall. The Plant Cell 15: 1399-1413; Voigt J, Woestemeyer J and Frank R (2007) The chaotrope-soluble glycoprotein GP2 is a precursor of the insoluble glycoprotein network of the *Chlamydomonas* cell wall. Journal of Biological Chemistry 282: 30381-30392.). These organisms and their relatives possess a distinct and unique type of cell wall based upon aggregates of hydroxyproline- and glycine-rich glycoproteins. In the well-studied representative, *Chlamydomonas reinhardtii*, 17-30 of these glycoproteins are found in the wall complex, arranged into interlocking fibrillar and granular elements. The walls of many of these organisms include crystalline layers. The hydroxyproline-rich glycoproteins are biochemically similar to extensins found in the cell walls of higher plants where they are involved in mechanostructural, regulatory and defense mechanisms. In the complex colonial flagellate Volvox, the extracellular matrix consists of at least four distinct zones and some of the inclusive glycoproteins are extensively sulfated. A few of these glycoproteins have elaborated into an extensive mucilaginous sheath, which holds daughter cells together. Other members of the Chlorophyta consist of diverse orders of nonmotile unicellular, coccoid and filamentous forms. The walls of many include the beta-1,4-glucan, cellulose, which is arranged in fibrils and is surrounded by a matrix sheath. In more primitive chlorophytan green algae (e.g. *Chlorella*), the microfibrils run in a random meshwork in that cellulose microfibril orientation is not preferentially oriented with respect to the cell surface. Some Chlorophytacontain certain matrix wall polysaccharides with considerable similarity to those found in land plants (Estevez J M, Leonardi P I and Alberghina J S (2008) Cell wall carbohydrate epitopes in the green alga *Oedogonium bharuchae F. minor* (Oedogoniales, Chlorophyta). Journal of Phycology 44: 1257-1268.). In addition, some unicellular members of the Chlorophyceae (e.g. the order of Chlorococcales) contain a 10-30-nm-wide, outer wall that has the appearance of a trilamellar sheath. This outer wall stratum is highly resistant to chemical hydrolysis and bacterial enzymatic degradation. The chemicals that make up this layer are called 'algaenans'. They consist of long polymethylenic chains associated with amide groups and minor amounts of N-alkyl substituted pyrroles. The role of algaenans appears to be a protective one, especially in conferring resistance to detergents (Corre G, Templier J, Largeau C, Rousseau B and Berkaloff C (1996) Influence of cell wall composition on the resistance of two *Chlorella* species (Chlorophyta) to detergents. Journal of Phycology 32: 584-590.). The ulvaphycean group of the Chlorophyta are represented by many different morphological types ranging from filaments (e.g. Urospora) to complex sheets of tissue The matrix polysaccharides surrounding the skeletal fibrillar complex in the Ulvaphyceae consists of an array of xylogalactoarabinans, glucuronoxylorhamnans (e.g. 'ulvan' sensu Ray B and Lahaye M (1995) Cell-wall polysaccharides from the marine green alga *Ulva 'rigida'* (Ulvales, Chlorophyta) Chemical structure of ulvan. Carbohydrate Research 274: 313-318.) and rhamnoxylogalactogalacturonans that are variously sulfated. The functions of the ulvaphycean matrix polysaccharides appear to be similar to matrix mucilages in other seaweeds like brown and red algae. Likewise, in some ulvaphycean forms, significant calcification occurs in the wall complex. In the coral reef alga Halimeda, crystals of aragonite encrust the cell wall to create a hard surface. The Streptophytan lineage of the green algae is often called the Charophyceae green algae (CGA). This lineage is most closely related and ancestral to land plants. Within this group are the stoneworts, *Chara* and Nitella, the desmids, filamentous conjugating-forms like Spirogyra, unique terrestrial forms like Klebsormidium (e.g. found on desert soils) and the highly advanced Coleochaete. The walls of most of the members of this group contain cellulosic skeletal components associated with various matrix-like macro-molecules (Sorensen I, Domozych D S and Willats W G T (2010) How have plant cell walls evolved? Plant Physiology 153: 366-372.; Popper Z A and Tuohy M G (2010) Beyond the green: understanding the evolutionary puzzle of plant and algal cell walls. Plant Physiology 153: 373-383.; Popper Z A (2008) Evolution and diversity of green plant cell walls. Current Opinion in Plant Biology 11: 286-292.; Popper Z A and Fry S C (2003) Primary cell wall composition of bryophytes and charophytes. Annals of Botany 91: 1-12; I.). In desmids, the microfibril orientation in the wall layers is similar to that of Valonia, except that no period of repetition can be seen in the direction of microfibrils throughout the succession of layers. In the stoneworts, microfibrils form an entangled meshwork that may run in a preferential orientation such as longitudinal, oblique or transverse with respect to the cell axis. Homogalacturonan-rich polysaccharides (e.g. pectins), xyloglucans, extensin and arabinogalactan proteins have also been found in the CGA (Domozych D S, Serfis A, Kiemle S N and Gret M R (2007) The structure and biochemistry of charophycean cell walls: I. Pectins of *Penium margaritaceum*. Protoplasma 230: 99-115., Domozych D S, Sorensen I and Willats W G T (2009a) The distribution of cell wall polymers during antheridium development and spermatogenesis in the Charophycean green alga, *Chara corallina*. Annals of Botany 104: 1045-1056., Domozych D S, Soerensen I, Pettolino F A, Bacic A and Willats W G T (2010) The cell wall polymers of the Charophycean green alga *Chara corallina*: immunobinding and biochemical screening. International Journal of Plant Sciences 171: 345-361.; Eder M and Lutz-Meindl U (2008) Pectin-like carbohydrates in the green alga *Micrasterias* characterized by cytochemical analysis and energy filtering TEM. Journal of Microscopy 231: 201-214.), suggesting significant similarity with matrix macromolecules of land plants. In some desmids, an extensive mucilage is released through pores in the cell wall, which in turn, causes the cell to glide. Likewise, these mucilages help the cell to adhere to substrates and may be involved in nutrient absorption and in interactions with beneficial bacteria. The mucilage is a glucuronic acid- and fucose-rich polysaccharide (Domozych et al., 2005; Domozych et al., 1993). Perhaps the closest charophycean ancestor to land plants among the green algae is Coleochaete. The walls of this alga consist of cellulose and matrix polysaccharides similar to that found in land plants. A cuticle-like outer coating has been identified on the cell surfaces and recently, lignin has been identified in the walls of this green alga (Soerensen, I, Pettolino, F. A. Bacic, A., Ralph, J., Lu, F., O'Neill, M. A., Fei, Z., Rose, J. K. C., Domozych, D. S., Willats, W. G. T. 2011. The Charophycean green algae provide insights into the early origins of plant cell walls. Plant Journal. Volume 68, Issue 2, October 2011, Pages 201-211).

Algal biomass should be understood in its broadest sense, so that it apart from intact algal cells also comprises different types of waste from industry and sewage plants. Biomass from several algae species contains high value added compounds like omega fatty acids and secondary metabolites like cartotinoids and isoprenoids and others. Algal cells are currently processed and fractioned in order to generate high added value compound depleted algal biomass, which is still a valuable feedstock for fermentative production of many compounds.

For example in a feasibility study lactic acid production from processed micro algal biomass using various lactic acid bacteria was already presented (Talukder, Md. M. R., Das, P. & Wu, J. C. (2012) Microalgae (*Nannochloropsis salina*) lipid. Biochemical Engineering Journal 68, 109-113). However as pointed out before, lactic bacteria require nutritional supplements, making the process expensive.

Algal biomass is a vast poorly exploited resource. However, hexoses derived from cell wall polymers can be converted by yeast to fuel ethanol for which there is a growing demand. Pentoses from xylan cannot be yet converted to ethanol commercially but several promising ethanologenic microorganisms with the capacity to convert pentoses and hexoses are under development.

Typically, the first step in utilization of algal biomass is a pre-treatment step, in order to reduce the crystallinity of the biomass and increase the surface area to enhance substrate digestibility.

The pre-treatment method often used is thermochemical treatment, a process heating of the algal material to a temperature of 100° C. for 8 h (Chen, P. and Oswald, W. (1998). Environmental International. 24. 889-897).

Another type of hydrolysis is alkaline hydrolysis (Razif Harun, W. S. Y. Jason, Tamara Cherrington, Michael K. Danquah. (2011). Exploring alkaline pre-treatment of microalgal biomass for bioethanol production. Applied Energy. 88. 3464-3467) where the algal material is subjected to an alkaline such as sodium hydroxide whereby the sugar polymers cellulose and others are partly or completely hydrolyzed to their constituent sugar monomers and the structure of the biomass is destroyed facilitating access of hydrolytic enzymes in subsequent processing steps.

Alternately a similar process can also be carried out with acids using 1% (v/v) of sulphuric acid for 30 min in combination with a thermochemical treatment at 140° C. (Razif Harun and Michael K. Danquah. (2011) Influence of acid pre-treatment on microalgal biomass for bioethanol production. Bioprocess Biochemistry. 46.304-309).

This pre-treatment step results in the hydrolysis of polymers like cellulose into glucose while xylan is transformed into the pentoses xylose. Thus, in contrast to starch, the hydrolysis of algal biomass results in the release of pentose sugars in addition to hexose sugars. This implies that useful fermenting organisms need to be able to convert both hexose and pentose sugars to desired fermentation products such as carboxylic acids.

After the pre-treatment the algal biomass processing schemes involving enzymatic or microbial hydrolysis commonly involve four biologically mediated transformations: (1) the production of saccharolytic enzymes (cellulases); (2) the hydrolysis of carbohydrate components present in pre-treated biomass to sugars; (3) the fermentation of hexose sugars (e.g. glucose); and (4) the fermentation of pentose sugars (e.g., xylose).

Each processing step can make the overall process more costly and, therefore, decrease the economic feasibility of producing biofuel or carbon-based chemicals from algal biological material. Thus, there is a need to develop methods that reduce the number of processing steps needed to convert algal biological material to biofuel or carbon-based chemicals and other commercially desirable materials.

Carboxylic acids are organic acids characterized by the presence of at least one carboxyl group. The general formula of a carboxylic acid is R—COOH, where R is some monovalent functional group. A carboxyl group (or carboxy) is a functional group consisting of a carbonyl (RR'C=O) and a hydroxyl (R—O—H), which has the formula —C(=O)OH, usually written as —COOH or —CO$_2$H. The term carboxylic acids includes salts and esters of the acids. Lactic acid is a carboxylic acid with the chemical formula C$_3$H$_6$O$_3$. It has a hydroxyl group adjacent to the carboxyl group, making it an alpha hydroxy acid (AHA).

In particular, these microorganisms are extremely thermophilic and show a broad substrate specificities and high natural production of carboxylic acids. Moreover, carboxylic acids fermentation at high temperatures, for example over 70° C. has many advantages over mesophilic fermentation. One advantage of thermophilic fermentation is the minimization of the problem of contamination in batch cultures, fed-batch cultures or continuous cultures, since only a few microorganisms are able to grow at such high temperatures in undetoxified algal biomass material.

It is also an advantage that the cells, strains and microorganisms according to the present disclosure grow on pre-treated as well as on untreated algal biomass material.

The isolated cells, strains, microorganisms, compositions and microbial cultures are capable of growing and producing fermentation products on very high dry-matter concentrations of algal biomass material.

In the present context the term "algal biomass material" is intended to designate an untreated algal biomass and/or an algal biomass which has been subjected to a pretreatment step whereby algal material has been at least partially separated into cellulose, pectins, xyloglucans, xylans, cellulose, mannans, xylans; agar and carageenans (sulfated galactans), lignin, acidic polysaccharides (alginates) thereby having increased the surface area and/or accessibility of the material. The algal material may typically be derived from intact algal cells or fractionated and processed algal cells, biomass from sewage plants, ponds, cultivations of photobioreactors and fermentors, seeweeds from aggradation of oceans and lakes.

The pretreatment method most often used is steam pretreatment, a process comprising heating of the algal material with or without steam injection to a temperature of 130-230 degrees centigrade with or without subsequent sudden release of pressure. Prior to or during steam pretreatment, a catalyst like a mineral or organic acid or a caustic agent facilitating disintegration of the biomass structure can be added optionally. Catalysts often used for such a pretreatment include but are not limited to sulphuric acid, sulphurous acid, hydrochloric acid, acetic acid, lactic acid, sodium hydroxide (caustic soda), potassium hydroxide, calcium hydroxide (lime), ammonia or the respective salts or anhydrides of any of these agents.

Such steam pretreatment step may or may not be preceded by another treatment step including cooking of the biomass in water or steaming of the biomass at temperatures of 100-200° C. with or without the addition of a suitable catalyst like a mineral or organic acid or a caustic agent facilitating disintegration of the biomass structure. In between the cooking step and the subsequent steam pretreatment step one or more liquid-solid-separation and washing steps can be introduced to remove solubilized algal biomass components in order to reduce or prevent formation of inhibitors during the subsequent steam pretreatment step.

Inhibitors formed during heat or steam pretreatment might include but are not limited to furfural formed from monomeric pentose sugars, hydroxymethylfurfural formed from monomeric hexose sugars, acetic acid, levulinic acid, phenols and phenol derivatives.

Another type of algal biomass hydrolysis is acid hydrolysis, where the algal material is subjected to an acid such as sulfuric acid or sulfurous acid whereby the sugar polymers cellulose and xylans are partly or completely hydrolyzed to their constituent sugar monomers.

A third method is wet oxidation wherein the material is treated with oxygen at 150-185 degrees centigrade. The pretreatments can be followed by enzymatic hydrolysis to complete the release of sugar monomers. This pre-treatment step results in the hydrolysis of cellulose into glucose while xylan is transformed into the pentose xylose. The pretreatment step may in certain embodiments be supplemented with treatment resulting in further hydrolysis of the cellulose and xylan. The purpose of such an additional hydrolysis treatment is to hydrolyze oligosaccharide and possibly polysaccharide species produced during the acid hydrolysis, wet oxidation, or steam pretreatment of cellulose and/or xylan origin to form fermentable sugars (e.g. glucose, xylose and possibly other monosaccharides). Such further treatments may be either chemical or enzymatic. Chemical hydrolysis is typically achieved by treatment with an acid, such as treatment with aqueous sulphuric acid or hydrochloric acid, at a temperature in the range of about 100-150 degrees centigrade. Enzymatic hydrolysis is typically performed by treatment with one or more appropriate carbohydrase enzymes such as cellulases, glucosidases and hemicellulases including xylanases.

It has been found that the microorganisms according to the present invention can grow efficiently on various species of pretreated and untreated algal biomass (e.g. green algae of the group of Chlorophyta e.g. *Nannochloropsis salina*).

The microorganisms according to the present disclosure also can grow efficiently on spent algal biomass—insoluble material that remains after a culture has grown to late stationary phase (e.g., greater than $10^8$ cells/mL) on untreated biomass.

Furthermore, the microorganisms according to the present disclosure grew efficiently on both the soluble and insoluble algal materials obtained after heat treating the biomass.

It was surprisingly found that the bacterial subspecies according to the present disclosure is capable of growing in a medium comprising algal biomass material having a dry matter content of at least 10 percent wt/wt, such as at least 15 percent wt/wt, including at least 20 percent wt/wt, and even as high as at least 25 percent wt/wt.

The used microorganisms according to the present disclosure are anaerobic thermophile bacteria, and they are capable of growing at high temperatures even at or above 70° C. The fact that the strains are capable of operating at this high temperature is of high importance in the conversion of the algal material into fermentation products. The conversion rate of carbohydrates into carboxylic acids is much faster when conducted at high temperatures. For example, the volumetric lactic acid productivity of a thermophilic *Bacillus* is up to ten-fold higher than a conventional yeast fermentation process which operates at 30 degrees centigrade. Consequently, a smaller production plant is required for a given plant capacity, thereby reducing plant construction costs. As also mentioned previously, the high temperature reduces the risk of contamination from other microorganisms, resulting in less downtime, increased plant productivity and a lower energy requirement for feedstock sterilization. The high operation temperature may also facilitate the subsequent recovery of the resulting fermentation products.

Algal biomass material and algal biomass hydrolysates might contain inhibitors such as furfural, phenols and carboxylic acids, which can potentially inhibit the fermenting organism. Therefore, it is an advantage of the microorganisms according to the present disclosure that they are tolerant to these inhibitors.

In advantageous embodiments, the microbial culture used in the methods according to the present disclosure comprises a thermophilic microorganism capable of surviving in high temperature conditions above 70° C.

In some embodiments, the algal biomass is contacted with a microbial culture for a period of time between 10 h to 300 h, preferably 50 h to 200 h, 80 h to 160 h, at an initial temperature between 55° C. and 80° C., preferably between 72° C. and 78° C. and at an initial pH between 5 and 9, preferably between 6 and 8.

In some embodiments, the thermophilic microorganism used in the methods according to the present disclosure is selected from the group consisting of *Clostridium thermocellum, Clostridium cellulolyticum, Thermoanaerobacterium saccharolyticum, Clostridium stercorarium, Clostridium stercorarium II, Caldicellulosiruptor kristjanssonii,* and *Clostridium phytofermentans, Thermoanaerobacterium thermosulfurigenes, Thermoanaerobacterium aotearoense, Thermoanaerobacterium poly saccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thertnocellum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, Caldicellulosiruptor acetigenus, Caldicellulosiruptor saccharolyticus, Caldi-*

*cellulosiruptor kristjanssonii, Caldicellulosiruptor owensensis, Caldicellulosiruptor lactoaceticus,* and *Anaerocellum thermophilum.*

In an advantageous embodiment, the used microorganisms according to the present disclosure are of the genus *Caldicellulosiruptor* or of the subspecies of *Caldicellulosiruptor saccharolyticus* (Vitali A Svetlitchnyi Oliver Kensch, Doris A Falkenhan, Svenja G Korseska, Nadine Lippert, Melanie Prinz, Jamaleddine Sassi, Anke Schickor and Simon Curvers. (2013) Single-step ethanol production from lignocelluloses using novel extremely thermophilic bacteria. Biotechnology for Biofuels 2013, 6:31).

For example, the genus *Caldicellulosiruptor* includes different species of extremely thermophilic (growth at temperature significantly above 70° C.) cellulolytic and hemicellulolytic strictly anaerobic non spore forming bacteria. The first bacterium of this genus, *Caldicellulosiruptor saccharolyticus* strain Tp8T (DSM 8903) has a temperature optimum of 70° C. and was isolated from a thermal spring in New Zealand (Rainey F A, Donnison A M, Janssen P H, Saul D, Rodrigo A, Bergquist P L, Daniel R M, Stackebrandt E, Morgan H W. (1994) Description of *Caldicellulosiruptor saccharolyticus* gen. 15 nov., sp. nov: an obligately anaerobic, extremely thermophilic, cellulolytic bacterium. FEMS Microbiol Lett. 120:263-266.; Sissons C H, Sharrock K R, Daniel R M, Morgan H W. (1987) Isolation of cellulolytic anaerobic extreme thermophiles from New Zealand thermal sites. Appl Environ Microbiol. 53:832-838). It hydrolyses a variety of polymeric carbohydrates with the production of acetate, lactate and trace amounts of ethanol (Donnison A M, Brockelsby C M, Morgan H W, Daniel R M. (1989) The degradation of lignocellulosics by extremely thermophilic microorganisms. Biotechnol Bioeng. 33:1495-1499). Phylogenetic analysis showed that it constitutes a novel lineage within the *Bacillus/Clostridium* subphylum of the Gram-positive bacteria (Rainey F A, Donnison A M, Janssen P H, Saul D, Rodrigo A, Bergquist P L, Daniel R M, Stackebrandt E, Morgan H W. (1994) Description of *Caldicellulosiruptor saccharolyticus* gen. nov., sp. nov: an obligately anaerobic, extremely thermophilic, cellulolytic bacterium. FEMS Microbiol Lett. 120:263-266).

According to the present disclosure, the microorganisms shown in table 1 and table 2 produce carboxylic acids like lactic acid and show several features: (i) high yield and low product inhibition, (ii) simultaneous utilization of algal biomass material and/or sugars, and (iii) growth at elevated temperatures. The used microorganisms according to the present disclosure are robust thermophile organisms with a decreased risk of contamination. They efficiently convert an extraordinarily wide range of biomass components to carboxylic acids like lactic acid and/or acetic acid.

Each independently an embodiment of the disclosure is the use of an isolated cell which is *Caldicellulosiruptor* sp. DIB004C (DSMZ Accession number 25177), an isolated cell which is *Caldicellulosiruptor* sp. DIB041C (DSMZ Accession number 25771), an isolated cell which is *Caldicellulosiruptor* sp. DIB087C (DSMZ Accession number 25772), an isolated cell which is *Caldicellulosiruptor* sp. DIB101C (DSMZ Accession number 25178), an isolated cell which is *Caldicellulosiruptor* sp. DIB103C (DSMZ Accession number 25773), an isolated cell which is *Caldicellulosiruptor* sp. DIB104C (DSMZ Accession number 25774) or an isolated cell which is *Caldicellulosiruptor* sp. DIB107C (DSMZ Accession number 25775), cells derived from either, mutants or a homolog of either.

In advantageous embodiments, the microorganism used in the methods according to the present disclosure belonging to the genus *Caldicellulosiruptor*, in particular the microorganism is selected from the group consisting of the microorganisms listed in table 1.

TABLE 1

| Genus | Species | Name | DSMZ accession number | Deposition date |
|---|---|---|---|---|
| Caldicellulosiruptor | sp. | DIB004C | DSM 25177 | Sep. 15, 2011 |
| Caldicellulosiruptor | sp. | DIB041C | DSM 25771 | Mar. 15, 2012 |
| Caldicellulosiruptor | sp. | DIB087C | DSM 25772 | Mar. 15, 2012 |
| Caldicellulosiruptor | sp. | DIB101C | DSM 25178 | Sep. 15, 2011 |
| Caldicellulosiruptor | sp. | DIB103C | DSM 25773 | Mar. 15, 2012 |
| Caldicellulosiruptor | sp. | DIB104C | DSM 25774 | Mar. 15, 2012 |
| Caldicellulosiruptor | sp. | DIB107C | DSM 25775 | Mar. 15, 2012 |

The strains listed in table 1 have been deposited in accordance with the terms of the Budapest Treaty on Sep. 15, 2011 with DSMZ—Deutsche Sammlung von Mikroorganismen and Zellkulturen GmbH, Inhoffenstr. 7B, 38124 Braunschweig, Germany, under the respectively indicated DSMZ accession numbers and deposition dates, respectively, by DIREVO Industrial Biotechnology GmbH, Nattermannallee 1, 50829 Cologne (DE).

The microorganisms of the species *Caldicellulosiruptor* sp. Used in the methods according to the present disclosure in particular refer to a microorganism which belongs to the genus *Caldicellulosiruptor* and which preferably has one or more of the following characteristics:

a) it is a microorganism of the genus *Caldicellulosiruptor*;

b) in a DNA-DNA hybridization assay, it shows a DNA-DNA relatedness of at least 70%, preferably at least 90%, at least 95%, more preferred at least 98%, most preferred at least 99% with either *Caldicellulosiruptor* sp. strain listed in table 1 with their respective accession numbers; and/or c) it displays a level of 16S rDNA gene sequence similarity of at least 98%, preferably at least 99% or at least 99.5%, more preferably 100% with either *Caldicellulosiruptor* sp. strain listed in table 1 with their respective accession numbers; and/or d) it is capable of surviving in high temperature conditions above 75° C.

e) it is capable of surviving in high temperature conditions above 70° C., and or f) it is a Gram-positive bacterium.

Preferably, at least two or at least three, and more preferred all of the above defined criteria a) to f) are fulfilled.

In an advantageous embodiment, the microorganisms used in a method according to the present disclosure in particular refer to a microorganism which belongs to the genus *Caldicellulosiruptor* and which preferably has one or more of the following characteristics:

a) It is a microorganism of the genus *Caldicellulosiruptor* b) it is a microorganism of the species *Caldicellulosiruptor saccharolyticus;* c) in a DNA-DNA hybridization assay, it shows a DNA-DNA relatedness of at least 80%, preferably at least 90%, at least 95%, more preferred at least 98%, most preferred at least 99%, and most preferred at least 99.9% with one of the strains of table 1; and/or d) it displays a level of 16S rDNA gene sequence similarity of at least 98%, preferably at least 99%, at least 99.5% or at least 99.7%, more preferably 99.99% with one of the strains listed in table 1; and/or e) it is capable of surviving and/or growing and/or producing a carboxylic acid at temperature conditions above 70° C., in particular of above 72° C.

Preferably, at least two or at least three, and more preferred all of the above defined criteria a) to e) are fulfilled.

The term "DNA-DNA relatedness" in particularly refers to the percentage similarity of the genomic or entire DNA of two microorganisms as measured by the DNA-DNA hybridization/renaturation assay according to De Ley et al. (1970) Eur. J. Biochem. 12, 133-142 or Huβ et al. (1983) Syst. Appl. Microbiol. 4, 184-192. In particular, the DNA-DNA hybridization assay preferably is performed by the DSMZ (Deutsche 5 Sammlung von Mikroorganismen and Zellkulturen GmbH, Braunschweig, Germany) Identification Service.

The term "16S rDNA gene sequence similarity" in particular refers to the percentage of identical nucleotides between a region of the nucleic acid sequence of the 16S ribosomal RNA (rDNA) gene of a first microorganism and the corresponding region of the nucleic acid sequence of the 16S rDNA gene of a second microorganism. Preferably, the region comprises at least 100 consecutive nucleotides, more preferably at least 200 consecutive nucleotides, at least 300 consecutive nucleotides or at least 400 consecutive nucleotides, most preferably about 480 consecutive nucleotides.

The strains according to disclosure have the potential to be capable of producing carboxylic acids like lactic acid and acetic acid.

The use of the *Caldicellulosiruptor* sp. strains according to the present disclosure have several highly advantageous characteristics needed for the conversion of algal biomass material. Thus, these base strains possess all the genetic machinery for the hydrolysis of cellulose and xylan and for the conversion of both pentose and hexose sugars to various fermentation products such as carboxylic acids like lactic acid. As will be apparent from the below examples, the examination of the complete 16S rDNA sequence showed that the closely related strains may all be related to *Caldicellulosiruptor saccharolyticus* although the 16S rDNA sequences may place them in a separate subspecies or even a different species.

In an advantageous embodiment, the *Caldicellulosiruptor* sp. microorganism used in a method according to the present disclosure is a) *Caldicellulosiruptor* sp. DIB004C, deposited on Sep. 15, 2011 under the accession number DSM 25177 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE), b) a microorganism derived from *Caldicellulosiruptor* sp. DIB004C or c) a *Caldicellulosiruptor* sp. DIB004C mutant.

In another preferred embodiment, the *Caldicellulosiruptor* sp. microorganism is a) *Caldicellulosiruptor* sp. DIB041C, deposited on Mar. 5 15, 2012 under the accession number DSM 25771 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE), b) a microorganism derived from *Caldicellulosiruptor* sp. DIB041C or c) a *Caldicellulosiruptor* sp. DIB041C mutant.

In another preferred embodiment, the *Caldicellulosiruptor* sp. microorganism used in a method according to the present disclosure is a) *Caldicellulosiruptor* sp. DIB087C, deposited on Mar. 15, 2012 under the accession number DSM 25772 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE), b) a microorganism derived from *Caldicellulosiruptor* sp. DIB087C or c) a *Caldicellulosiruptor* sp. DIB087C mutant.

In another preferred embodiment, the *Caldicellulosiruptor* sp. microorganism used in a method according to the present disclosure is a) *Caldicellulosiruptor* sp. DIB101C, deposited on Sep. 15, 2011 under the accession number DSM 25178 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE), b) a microorganism derived from *Caldicellulosiruptor* sp. DIB101C or c) a *Caldicellulosiruptor* sp. DIB101C mutant.

In another preferred embodiment, the *Caldicellulosiruptor* sp. microorganism used in a method according to the present disclosure is a) *Caldicellulosiruptor* sp. DIB103C, deposited on Mar. 15, 2012 under the accession number DSM 25773 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE), b) a microorganism derived from *Caldicellulosiruptor* sp. DIB103C or c) a *Caldicellulosiruptor* sp. DIB103C mutant.

In another preferred embodiment, the *Caldicellulosiruptor* sp. microorganism used in a method according to the present disclosure is a) *Caldicellulosiruptor* sp. DIB104C, deposited on Mar. 15, 2012 under the accession number DSM 25774 according to the requirements of the Budapest Treaty at the Deutsche 10 Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE), b) a microorganism derived from *Caldicellulosiruptor* sp. DIB104C or c) a *Caldicellulosiruptor* sp. DIB104C mutant.

In another preferred embodiment, the *Caldicellulosiruptor* sp. microorganism used in a method according to the present disclosure is a) *Caldicellulosiruptor* sp. DIB107C, deposited on Mar. 15, 2012 under the accession number DSM 25775 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE), b) a microorganism derived from *Caldicellulosiruptor* sp. DIB107C or c) a *Caldicellulosiruptor* sp. DIB107C mutant.

All strains listed above and in table 1 belong to the genus *Caldicellulosiruptor* and are strictly anaerobic, non-sporeforming, non-motile, gram-positive bacteria. Cells are straight rods 0.4-0.5 μm by 2.0-4.0 μm, occurring both singly and in pairs. After 7 days incubation at 72° C. on solid medium with agar and cellulose as substrate both strains form circular milky colonies of 0.5-1 mm in diameter. Clearing zones around the colonies are produced indicating cellulose degradation.

The term "a microorganism" as used herein may refer to only one unicellular organism as well as to numerous single unicellular organisms. For example, the term "a microorganism of the genus *Caldicellulosiruptor*" may refer to one single *Caldicellulosiruptor* bacterial cell of the genus *Caldicellulosiruptor* as well as to multiple bacterial cells of the genus *Caldicellulosiruptor*.

The terms "a strain of the genus *Caldicellulosiruptor*" and "a *Caldicellulosiruptor* cell" are used synonymously herein. In general, the term "a microorganism" refers to numerous cells. In particular, said term refers to at least $10^3$ cells, preferably at least $10^4$ cells, at least $10^5$ or at least $10^6$ cells.

In other advantageous embodiments, another microorganism used in the methods according to the present disclosure is a microorganism of the genus *Thermoanaerobacter*. The *Thermoanaerobacter* sp. strains according to the present disclosure as listed in table 2 are saccharolytic (ferment hexoses and pentoses to ethanol, lactate and traces of acetate). Five strains listed in table 2 are related to *Thermoanaerobacter mathranii* and three strains are related to *Thermoanaerobacter thermohydrosulfuricus*.

For example, the genus *Thermoanaerobacter* includes different species of extremely thermophilic (temperature optima for growth higher than 70° C.) and thermophilic hemicellulolytic and saccharolytic strictly anaerobic bacteria (Lee et al. 1993). *Thermoanaerobacter mathranii* DSM 11426 is an extremely thermophilic bacterium. It has a temperature optimum between 70 and 75° C. and was isolated from a hot spring in Iceland (Larsen et al. 1997). It uses a number of sugars as carbon sources, but did not utilize microcrystalline cellulose. Fermentation end products on xylose were ethanol, acetate, low amounts of lactate, $CO_2$, and $H_2$ (Larsen et al. 1997). *Thermoanaerobacter brockii* subsp. *finnii* is a thermophilic saccharolytic bacterium. It has a temperature optimum between 55 and 60° C. and was isolated from an oil field at a depth of 2,100 m (Cayol et al. 1995). It uses a number of sugars as carbon sources, but cannot utilize xylan or cellulose. Fermentation end products on glucose were lactate, acetate, ethanol, $H_2$, and $CO_2$ (Coyol et al. 1995).

In advantageous embodiments, the microorganism used in the methods according to the present disclosure belonging to the genus *Thermoanaerobacter* and is selected from the group consisting of the microorganisms listed in table 2.

TABLE 2

| Genus | Species | Name | DSMZ accession number | Deposition date |
|---|---|---|---|---|
| *Thermoanaerobacter* | sp. | DIB004G | DSM 25179 | 15 Sep. 2011 |
| *Thermoanaerobacter* | sp. | DIB087G | DSM 25777 | 15 Mar. 2012 |
| *Thermoanaerobacter* | sp. | DIB097X | DSM 25308 | 27 Oct. 2011 |
| *Thermoanaerobacter* | sp. | DIB101G | DSM 25180 | 15 Sep. 2011 |
| *Thermoanaerobacter* | sp. | DIB101X | DSM 25181 | 15 Sep. 2011 |
| *Thermoanaerobacter* | sp. | DIB103X | DSM 25776 | 15 Mar. 2012 |
| *Thermoanaerobacter* | sp. | DIB104X | DSM 25778 | 15 Mar. 2012 |
| *Thermoanaerobacter* | sp. | DIB107X | DSM 25779 | 15 Mar. 2012 |

The strains listed in table 2 have been deposited in accordance with the terms of the Budapest Treaty on the notified deposition dates with DSMZ—Deutsche Sammlung von Mikroorganismen and Zellkulturen GmbH, Inhoffenstr. 7B, 38124 Braunschweig, Germany, under the above notified DSMZ accession numbers by DIREVO Industrial Biotechnology GmbH, Nattermannallee 1, 50829 Cologne (DE).

In an advantageous embodiment, *Thermoanaerobacter* sp. DIB004G (DSMZ Accession number 25179) and/or *Thermoanaerobacter* sp. DIB101G (DSMZ Accession number 25180), cells derived there from, mutants there from, progenies or homologs are used in the production methods according to the present disclosure.

In further embodiments, the algal biomass is contacted and/or treated with a microorganism having one or more of the following characteristics:
  a) it is a microorganism of the genus *Thermoanaerobacter*; and/or
  b) in a DNA-DNA hybridization assay, it shows a DNA-DNA relatedness of at least 70%, preferably at least 90%, at least 95%, more preferred at least 98%, most preferred at least 99% with any of the *Thermoanaerobacter* sp. strains listed in table 2 with the respectively indicated accession numbers and deposition dates; and/or
  c) it displays a level of 16S rDNA gene sequence similarity of at least 98%, preferably at least 99% or at least 99.5%, more preferably 100% with any of the *Thermoanaerobacter* sp. strains listed in table 2 with the respectively indicated accession numbers and deposition dates, respectively; and/or
  d) it is capable of growing in high temperature conditions above 70° C., and/or
  e) it is a Gram-positive bacterium.

Preferably, at least two or at least three, and more preferred all of the above defined criteria a) to e) are fulfilled.

In another advantageous embodiment, the microorganism used in the methods according to the present disclosure is:
  a) *Thermoanaerobacter* sp. DIB004G, deposited on Sep. 15, 2011 under the accession number DSM 25179 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne, Germany (DE), or
  b) a microorganism derived from *Thermoanaerobacter* sp. DIB004G, or
  c) a *Thermoanaerobacter* sp. DIB004G homolog.

In another advantageous embodiment, the microorganism used in the methods according to the present disclosure is:
  a) any *Thermoanaerobacter* sp. strain except *Thermoanaerobacter* sp. DIB004G listed in table 2 with their respectively indicated deposition dates and accession numbers deposited according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne, Germany (DE), or
  b) a microorganism derived from either of these *Thermoanaerobacter* sp. strains or
  c) a homolog of either of these strains All *Thermoanaerobacter* sp. strains listed in table 2 belong to the genus *Thermoanaerobacter* and are extremely thermophilic (growth at temperatures higher than 70° C.), saccharolytic, strictly anaerobic and Gram-positive bacteria. Cells are straight rods 0.3-0.4 μm by 2.0-6.0 μm, occurring both singly and in pairs.

In a further embodiment, *Thermoanaerobacter* sp. DIB101X deposited as DSM 25181 and/or *Thermoanaerobacter* sp. DIB97X deposited as DSM 25308, cells derived there from, mutants there from, progenies or homologs are used as the microorganism in the production methods according to the present disclosure.

The strain DIB101X has been deposited in accordance with the terms of the Budapest Treaty on Sep. 15, 2011 with DSMZ—Deutsche Sammlung von Mikroorganismen und Zellkulturen GmbH, Inhoffenstr. 7B, 38124 Braunschweig, Germany under DSMZ accession number DSM 25181 by DIREVO Industrial Biotechnology GmbH, Nattermannallee 1, 50829 Cologne, Germany (DE).

The strain DIB97X has been deposited in accordance with the terms of the Budapest Treaty on Oct. 27, 2011 with DSMZ—Deutsche Sammlung von Mikroorganismen und Zellkulturen GmbH, Inhoffenstr. 7B, 38124 Braunschweig, Germany under DSMZ accession number DSM 25308 by DIREVO Industrial Biotechnology GmbH, Nattermannallee 1, 50829 Cologne, Germany (DE).

In further embodiments, the algal biomass is contacted and/or treated with a microorganism having one or more of the following characteristics:

a) it is a microorganism of the genus *Thermoanaerobacter*; and/or
b) in a DNA-DNA hybridization assay, it shows a DNA-DNA relatedness of at least 70%, preferably at least 90%, at least 95%, more preferred at least 98%, most preferred at least 99% with *Thermoanaerobacter* sp. DIB101X or *Thermoanaerobacter* sp. DIB97X deposited as DSM 25181 or DSM 25308, respectively; and/or
c) it displays a level of 16S rDNA gene sequence similarity of at least 98%, preferably at least 99% or at least 99.5%, more preferably 100% with *Thermoanaerobacter* sp. DIB101X or *Thermoanaerobacter* sp. DIB97X deposited as DSM 25181 or DSM 25308, respectively; and/or
d) it is capable of growing in high temperature conditions above 70° C., and/or
e) it is a Gram-positive bacterium.

Preferably, at least two or at least three, and more preferred all of the above defined criteria a) to e) are fulfilled.

In another advantageous embodiment, the microorganism used in the methods according to the present disclosure is:
d) *Thermoanaerobacter* sp. DIB101X, deposited on Sep. 15, 2011 under the accession number DSM 25181 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne, Germany (DE), or
e) a microorganism derived from *Thermoanaerobacter* sp. DIB101X, or
f) a *Thermoanaerobacter* sp. DIB101X homolog.

In another advantageous embodiment, the second microorganism used in the methods according to the present disclosure is:
d) *Thermoanaerobacter* sp. DIB97X, deposited on Oct. 27, 2011 under the accession number DSM 25308 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne, Germany (DE), or
e) a microorganism derived from *Thermoanaerobacter* sp. DIB97X or
f) a *Thermoanaerobacter* sp. DIB97X homolog.

*Thermoanaerobacter* sp. DIB101X (DSM 25181) and DIB97X (DSM 25308) belong to the genus *Thermoanaerobacter* and are extremely thermophilic (growth at temperatures higher than 70° C.), xylanolytic and saccharolytic, strictly anaerobic, Gram-positive bacteria. Cells are straight rods 0.3-0.4 µm by 2.0-6.0 µm, occurring both singly and in pairs. DIB101X and DIB97X grow on various sugars as substrate, including xylan, xylose, cellobiose, and glucose.

As is apparent from the following, the preferred strains of the present disclosure have been deposited. Other cells, strains, bacteria, microorganisms and/or microbial cultures of the present disclosure can therefore be obtained by mutating the deposited strains and selecting derived mutants having enhanced characteristics. Desirable characteristics include an increased range of sugars that can be utilized, increased growth rate, ability to produce higher amounts of carbon-based chemicals such as lactic acid. Suitable methods for mutating bacteria strains and selecting desired mutants are described in Functional analysis of Bacterial genes: A practical Manual, edited by W. Schumann, S. D. Ehrlich & N. Ogasawara, 2001.

In advantageous embodiments the microorganisms may be modified in order to obtain mutants or derivatives with improved characteristics. Thus, in one embodiment there is provided a bacterial strain according to the disclosure, wherein one or more genes have been inserted, deleted or substantially inactivated. The variant or mutant is typically capable of growing in a medium comprising a algal biomass.

The strains according to the disclosure are strictly anaerobic microorganisms, and hence it is preferred that the fermentation product is produced by a fermentation process performed under strictly anaerobic conditions. Additionally, the microorganisms according to the disclosure are extremely thermophillic microorganisms, and therefore the process may perform optimally, when it is operated at temperature in the range of about 45-95 degrees centigrade, such as the range of about 50-90 degrees centigrade, including the range of about 60-85 degrees centigrade, such as the range of about 65-75 degrees centigrade. In an advantageous embodiment the temperature is 70° C. and higher.

For the production of certain fermentation products, it may be useful to select a specific fermentation process, such as batch fermentation process, including a fed-batch process or a continuous fermentation process. Also, it may be useful to select a fermentation reactor such as an immobilized cell reactor, a fluidized bed reactor or a membrane bioreactor.

In some advantageous embodiments the algal biomass is derived from green algae, in from algae of the class chlorophyceae, preferably of the order chlamydomonadales, preferably of the family haematococcaceae, more preferably of the genus *haematococcus* like *Haematococcus pluvialis*.

As mentioned above algal biomass according to the present invention can be but is not limited to the cells of the algal taxa Chlorophyta and Streptophyta (green algae), Rhodophyta (red algae), Haptophyta and Haptophytes, Ochrophytes, Synurophytes, Synurophyceae, Bacillarophyceae (diatoms), Phaeophyta (brown algae) and Dinophyta (Dinoflagellates), algae cake from oil or fine chemical extraction processes and algal biomass material obtained through processing of algal cells. In advantageous embodiments, the algal biomass is cells of the taxon Chlorophyta, preferably *Nannochloropsis salina*.

In advantageous embodiments, the algal biomass material is subjected to mechanical, thermochemical, and/or biochemical pretreatment. The algal biomass material could be exposed to steam treatment. In further embodiments, the algal biomass material is pretreated with mechanical comminution and a subsequent treatment with lactic acid, acetic acid, sulfuric acid or sulfurous acid or their respective salts or anhydrides under heat and pressure with or without a sudden release of pressure. In another embodiment, the algal biomass material is pretreated with mechanical comminution and a subsequent treatment with either sodium hydroxide, ammonium hydroxide, calcium hydroxide or potassium hydroxide under heat and pressure with or without a sudden release of pressure.

In advantageous embodiments, the algal biomass material is pretreated with mechanical comminution and subsequent exposure to a multi-step combined pretreatment process. Such multi-step combined pretreatment may include a treatment step consisting of cooking in water or steaming of the algal biomass material at a temperature of 100-200° C. for a period of time in between 5 and 120 min. Suitable catalysts including but not limited to lactic acid, acetic acid, sulfuric acid, sulfurous acid, sodium hydroxide, ammonium hydroxide, calcium hydroxide or potassium hydroxide or their respective salts or anhydrides may or may not be added to the process. The process may further include a step comprising a liquid-solid separation operation, e.g. filtration, separation, centrifugation or a combination thereof, separating the process fluid containing partially or fully hydrolyzed and solubilized constituents of the algal biomass material from the remaining insoluble parts of the algal biomass. The process may further include a step comprising washing of the remaining algal biomass material. The solid material separated from solubilized algal biomass constituents may then be treated in a second step with steam under heat and pressure with or without a sudden release of pressure at a temperature of 150-250° C. for a period of time in between 1 and 15 min. In order to increase pretreatement effectiveness, a suitable catalyst including but not limited to lactic acid, acetic acid, sulfuric acid, sulfurous acid, sodium hydroxide, ammonium hydroxide, calcium hydroxide or potassium hydroxide or their respective salts or anhydrides may be added also to the second step.

In advantageous embodiments, the algal biomass is milled before converted into carboxylic acids like lactic acid. In one embodiment, the algal biomass is pretreated biomass from *Nannochloropsis salina*, preferably pretreated with steam pretreatment or multi-step combined pretreatment.

In advantageous embodiments the cells, strains, microorganisms may be modified in order to obtain mutants or derivatives with improved characteristics. Thus, in one embodiment there is provided a bacterial strain according to the disclosure, wherein one or more genes have been inserted, deleted or substantially inactivated. The variant or mutant is typically capable of growing in a medium comprising a lignocellulosic biomass material.

In another embodiment, there is provided a process for preparing variants or mutants of the microorganisms according to the present disclosure, wherein one or more genes are inserted, deleted or substantially inactivated as described herein.

In some embodiments one or more additional genes are inserting into the strains according to the present disclosure. Thus, in order to improve the yield of the specific fermentation product, it may be beneficial to insert one or more genes encoding a polysaccharase into the strain according to the invention. Hence, in specific embodiments there is provided a strain and a process according to the invention wherein one or more genes encoding a polysaccharase which is selected from cellulases (such as EC 3.2.1.4); beta-glucanases, including glucan-1,3 beta-glucosidases (exo-1,3 beta-glucanases, such as EC 3.2.1.58), 1,4-beta-cellobiohydrolases (such as EC 3.2.1.91) and endo-1,3(4)-beta-glucanases (such as EC 3.2.1.6); xylanases, including endo-1,4-beta-xylanases (such as EC 3.2.1.8) and xylan 1,4-beta-xylosidases (such as EC 3.2.1.37); pectinases (such as EC 3.2.1.15); alphaglucuronidases, alpha-L-arabinofuranosidases (such as EC 3.2.1.55), acetylesterases (such as EC 3.1.1.-), acetylxylanesterases (such as EC 3.1.1.72), alpha-amylases (such as EC 3.2.1.1), beta-amylases (such as EC 3.2.1.2), glucoamylases (such as EC 3.2.1.3), pullulanases (such as EC 3.2.1.41), beta-glucanases (such as EC 3.2.1.73), hemicellulases, arabinosidases, mannanases including mannan endo-1,4-beta-mannosidases (such as EC 3.2.1.78) and mannan endo-1,6-alpha-mannosidases (such as 5 EC 3.2.1.101), pectin hydrolases, polygalacturonases (such as EC 3.2.1.15), exopolygalacturonases (such as EC 3.2.1.67) and pectate lyases (such as EC 4.2.2.10), are inserted.

In accordance with the present disclosure, a method of producing a fermentation product comprising culturing a strain according to the invention under suitable conditions is also provided.

The strains according to the disclosure are strictly anaerobic microorganisms, and hence it is preferred that the fermentation product is produced by a fermentation process performed under strictly anaerobic conditions. Additionally, the strain according to invention is an extremely thermophillic microorganism, and therefore the process may perform optimally, when it is operated at temperature in the range of about 40-95° C., such as the range of about 50-90° C., including the range of about ° C. degrees centigrade, such as the range of about 65-75° C. In an advantageous embodiment the process is operated at 72° C.

For the production of certain fermentation products, it may be useful to select a specific fermentation process, such as batch fermentation process, including a fed-batch process or a continuous fermentation process. Also, it may be useful to select a fermentation reactor such as a stirred vessel reactor, an immobilized cell reactor, a fluidized bed reactor or a membrane bioreactor.

In accordance with the invention, the method is useful for the production of a wide range of carboxylic acids such as lactic acid and acetic acid may be produced in accordance with the invention.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

The following methods and examples are offered for illustrative purposes only, and are not intended to limit the scope of the present disclosure in any way.

METHODS AND EXAMPLES

In the following examples, materials and methods of the present disclosure are provided including the determination of the properties of the microbial strains according to the present disclosure. It should be understood that these examples are for illustrative purpose only and are not to be construed as limiting this disclosure in any manner. All publications, patents, and patent applications cited herein are hereby incorporated by reference in their entirety for all purposes.

Example 1: Isolation and Cultivation

All procedures for enrichment and isolation of the strains listed in table 1 employed anaerobic technique for strictly anaerobic bacteria (Hungate R E. (1969) A roll tube method for cultivation of strict anaerobes. In: Methods in Microbiology Eds. Norris J R and Ribbons D W. pp 118-132. New York: Academic Press). The strains were enriched from environmental samples at temperatures higher than 70° C. with beech wood as substrate. Isolation was performed by picking colonies grown on solid agar medium at 72° C. in Hungate roll tubes (Hungate R E. (1969) A roll tube method for cultivation of strict anaerobes. In: Methods in Microbiology Eds. Norris J R and Ribbons D W. pp 118-132. New York: Academic Press). The cells are cultured under strictly anaerobic conditions applying the following medium:

| Basic medium | | |
|---|---|---|
| $NH_4Cl$ | 1.0 | g |
| NaCl | 0.5 | g |
| $MgSO_4 \times 7\ H_2O$ | 0.3 | g |
| $CaCl_2 \times 2\ H_2O$ | 0.05 | g |
| $NaHCO_3$ | 0.5 | g |
| $K_2HPO_4$ (in bottles 2x; Hungate roll tubes 2x) | 1.5 | g |
| $KH_2PO_4$ (in bottles 2x; Hungate roll tubes 2x) | 3.0 | g |
| Yeast extract (bacto, BD) | 0.5 | g |
| Cellobiose | 5.0 | g |
| Vitamins (see below) | 1.0 | ml |
| Trace elements (see below) | 0.5 | ml |
| Resazurin | 1.0 | mg |
| $Na_2S \times 9\ H_2O$ | 0.75 | g |
| Distilled water | 1000.0 | ml |

| Trace elements stock solution | | |
|---|---|---|
| $NiCl_2 \times 6H_2O$ | 2 | g |
| $FeSO_4 \times 7H_2O$ | 1 | g |
| $NH_4Fe(III)$ citrate, brown, 21.5% Fe | 10 | g |
| $MnSO_4 \times H_2O$ | 5 | g |
| $CoCl_2 \times 6H_2O$ | 1 | g |
| $ZnSO_4 \times 7H_2O$ | 1 | g |
| $CuSO_4 \times 5H_2O$ | 0.1 | g |
| $H_3BO_3$ | 0.1 | g |
| $Na_2MoO_4 \times 2H_2O$ | 0.1 | g |
| $Na_2SeO_3 \times 5H_2O$ | 0.2 | g |
| $Na_2WoO_4 \times 2H_2O$ | 0.1 | g |
| Distilled water 1000.0 ml | 1000.0 | ml |
| Add 0.5 ml of the trace elements stock solution to 1 liter of the medium | | |

| Vitamine stock solution | | |
|---|---|---|
| nicotinic acid | 200 | mg |
| cyanocobalamin | 25 | mg |
| p-aminobenzoic acid (4-aminobenzoic acid) | 25 | mg |
| calcium D-pantothenate | 25 | mg |
| thiamine-HCl | 25 | mg |
| riboflavin | 25 | mg |
| lipoic acid | 25 | mg |
| folic acid | 10 | mg |
| biotin | 10 | mg |
| pyridoxin-HCl | 10 | mg |
| Distilled water | 200.0 | ml |
| Add 1 ml of the vitamine stock solution to 1 liter of the medium | | |

All ingredients except sulfide are dissolved in deionized water and the medium is flushed with nitrogen gas (purity 99,999%) for 20 min at room temperature. After addition of sulfide, the pH-value is adjusted to 7.0 at room temperature with 1 M HCl. The medium is then dispensed into 16 ml Hungate tubes (with 8 ml medium) or 200 ml serum bottles with (100 ml medium) under nitrogen atmosphere and the vessels are tightly sealed. After autoclaving at 121° C. for 20 min pH-value should be in between 6.8 and 7.0.

Carbon sources are added prior to autoclaving. Subsequent to autoclaving, cultures are inoculated by injection of a seed culture through the seal septum and inoculated in an incubator at 72° C. for about 18 hours.

For generation of a pre cultures for fermentation experiments first 16 ml Hungate tubes (filled with 8 ml medium) containing 4.3 g/l of cellulose (strips of filter paper Whatman No. 1) and 20 g/l of untreated ground beech wood as substrate were inoculated and then incubated at 72° C. for 18 hours and then 8 ml of this preculture was inoculated in 200 ml serum bottles with (100 ml medium containing 1% microcrystalline cellulose) and cultivated at 72° C. for 18 hours.

Example 2: HPLC

Sugars and fermentation products were quantified by HPLC-RI using a Via Hitachi LaChrom Elite (Hitachi corp.) fitted with a Rezex ROA Organic Acid H+(Phenomenex). The analytes were separated isocratically with 2.5 mM $H_2SO_4$ and at 65° C.

Example 3: Fermentation Algal Biomass

A batch experiment with strain DIB104C (10% inoculation; 14 ml) was performed by cultivation in double jacketed glass cultivation vessel (140 ml working volume) on the medium described above (except for replacing of $Na_2S \times 9H_2O$ 0.75 g/L by $Na_2SO_3$ 0.5 g/L) with addition of 60 g cell paste (consisting of 33.3% dry weight i.e. 20 g dry weight)/L of the untreated green algae Nannochloropsis salina. The vessel was inoculated with 14 ml (final volume 10%) of a seed preculture which had been inoculated in 200 ml serum bottles with (100 ml medium containing 1% microcrystalline cellulose), which were cultivated at 72° C. for 18 hours.

Temperature was controlled to 70° C. and the pH-value was controlled to 6.75±0.1 throughout the fermentation by titration with 2M NaOH. The fermenter was purged with nitrogen to remove excess oxygen before sodium sulphite was added as described above.

The fermentation was started by addition of a seed culture prepared as described before. A sample was taken after 120 hours cultivation time, then the sample was centrifuged at 14000 g and then the supernatant was analyzed by HPLC. The results of the HPLC analysis as described in Table 3 show parallel production of lactate (0.8 mM) and acetate (16.6 mM) pointing out the production of carboxylic acids from algal biomass.

TABLE 3

| Strain | Substrate | Incubation time h | Lactate formed mM | Acetate formed mM |
|---|---|---|---|---|
| DIB104C | Algal biomass Nannochloropsis salina (2% dry weight/L) | 120 | 0.8 | 16.6 |

In Table 4 the results from another example for the production of lactic acid, acetic acid and ethanol by the strain DIB104C after 120 h growth on untreated algal biomass of the green alga species *Nannochloropsis salina* are shown.

Examples 4: Cultivations on Algal Biomass in Serum Bottles

Batch experiments with strain DIB104C (1% inoculation; 1 ml) in 200 ml serum bottles (contain 100 ml medium) on the medium described above (except for leaving out yeast extract as a carbon source) with addition of 30 g cell paste (consisting of 33.3% dry weight i.e. 10 g dry weight)/L of the untreated or autoclaved (121° C., 20 minutes, 1.2 bar (=120 kPa)) green algae *Nannochloropsis salina*. The serum bottles were inoculated with 1 ml (final volume 10%) of a seed preculture, which had been inoculated in 200 ml serum bottles with 100 ml medium containing 1% microcrystalline cellulose at 72° C. for 18 hours. Control serum bottles (without DIB104C) were generated using the same medium (containing untreated or autoclaved algae biomass) like the ones, which were inoculated, but inoculating by DIB104C was omitted.

The inoculated and not inoculated serum bottles were incubated in parallel at 72° C. at 100 rpm in a laboratory flask shaker. The cultivation was started by addition of a seed culture prepared as described before. A sample was taken after 77.5 hours cultivation time, then the sample was centrifuged at 14000 g and then the supernatant was analyzed by HPLC. The results of the HPLC analysis as described in table 4 and table 5 show parallel productions of lactate, acetate and ethanol. For analysis of the production of the carbon based chemicals lactate, acetate and ethanol by DIB104C on algal biomass the results of the inoculated serum flasks were subtracted from the results of the control serum flasks (not inoculated). The results of this calculation shows production of lactate (0.3 mM), acetate (4.1 mM) and ethanol (0.8 mM) by DIB104C on untreated algal biomass and production of lactate (0.5 mM), acetate (7.9 mM) and ethanol (0.6 mM) by the DIB104C on autoclaved algal biomass pointing out the production of carbon based chemicals from untreated and autoclaved algal biomass.

TABLE 4

| Strain | Substrate | Incubation time h | Lactate concentration mM | Acetate concentration mM | Ethanol concentration mM |
|---|---|---|---|---|---|
| DIB104C | untreated algal biomass *Nannochloropsis salina* (1% dry weight/L) | 77.5 | 0.3 | 4.8 | 1.7 |
| Control: without DIB104C | untreated algal biomass *Nannochloropsis salina* (1% dry weight/L) | 77.5 | 0 | 0.7 | 0.9 |
| | | | Lactate formed by DIB104C [mM] | Acetate formed by DIB104C [mM] | Ethanol formed by DIB104C [mM] |
| | | | 0.3 | 4.1 | 0.8 |

TABLE 5

| Strain | Substrate | Incubation time h | Lactate concentration mM | Acetate concentration mM | Ethanol concentration mM |
|---|---|---|---|---|---|
| DIB104C | Autoclaved algal biomass *Nannochloropsis salina* (1% dry weight/L) | 77.5 | 0.5 | 9.1 | 2.1 |
| Control: without DIB104C | Autoclaved algal biomass *Nannochloropsis salina* (1% dry weight/L) | 77.5 | 0 | 1.2 | 1.5 |
| | | | Lactate formed by DIB104C [mM] | Acetate formed by DIB104C [mM] | Ethanol formed by DIB104C [mM] |
| | | | 0.5 | 7.9 | 0.6 |

Examples 5: Cultivations on Dried Algal Biomass in Serum Bottles

Batch experiments with strain DIB104C (1% inoculation; 1 ml) in 200 ml serum bottles (contain 100 ml medium) on the medium described above (including yeast extract as a carbon source) with addition of 10 g lyophilized (i.e. 10 g dry weight)/L of the autoclaved (121° C., 20 minutes, 1.2 bar (=120 kPa)) green algae *Nannochloropsis salina*. The serum bottles were inoculated with 1 ml (final volume 10%) of a seed preculture, which had been inoculated in 200 ml serum bottles with 100 ml medium containing 1% microcrystalline cellulose at 72° C. for 30 hours and shaken at 100 rpm. Control serum bottles (without DIB104C) were generated using the same medium (containing autoclaved lyophilized algae biomass) like the ones, which were inoculated, but inoculating by DIB104C was omitted. For the experiments three parallel sets of serum bottles inoculated by DIB104C and three parallel sets of serum bottles not inoculated by DIB104C (controls) were used.

The inoculated and not inoculated serum bottles were incubated in parallel at 72° C. at 100 rpm in a laboratory flask shaker. The cultivation was started by addition of a seed culture prepared as described before. Samples were taken after 0, 17, 22, 39, 63 and 134 hours cultivation time, then the sample was centrifuged at 14000 g and then the supernatant was analyzed by HPLC. The results of the HPLC analysis reflected as the average of the three serum bottles as described in table 6 and in table 7 show parallel productions of acetate and ethanol. For analysis of the production of the carbon based chemicals acetate and ethanol by DIB104C on algal biomass the results of the inoculated serum flasks were subtracted from the results of the control serum flasks (not inoculated).

The results of this calculation shows production of acetate (6.0 mM) and ethanol (0.5 mM) after 134 hour cultivation by DIB104C on lyophilized and autoclaved algal biomass pointing out the production of carbon based chemicals from lyophilized and autoclaved algal biomass.

TABLE 6

| Incubation time [h] | Acetate concentration with DIB104C [mM] | Acetate concentration without DIB104C (control) [mM] | Acetate formed by DIB104C [mM] |
| --- | --- | --- | --- |
| 0 | 1.2 | 1.2 | <0.1 |
| 17 | 6.0 | 1.3 | 4.7 |
| 22 | 6.6 | 1.3 | 5.3 |
| 39 | 7.0 | 1.3 | 5.7 |
| 63 | 7.3 | 1.3 | 6.0 |
| 134 | 7.4 | 1.4 | 6.0 |

TABLE 7

| Incubation time [h] | Ethanol concentration with DIB104C [mM] | Ethanol concentration without DIB104C (control) [mM] | Ethanol formed by DIB104C [mM] |
| --- | --- | --- | --- |
| 0 | 1.3 | 1.3 | <0.1 |
| 17 | 1.6 | 1.4 | 0.2 |
| 22 | 1.6 | 1.4 | 0.2 |
| 39 | 1.7 | 1.4 | 0.3 |
| 63 | 1.8 | 1.4 | 0.4 |
| 134 | 1.9 | 1.4 | 0.5 |

What is claimed is:

1. A method of producing lactic acid or a salt or an ester thereof from algal biomass material converting the algal biomass material to lactic acid in a single step process, the method comprising:
 a. culturing and growing algae in a liquid medium to a desired algae biomass;
 b. combining a microbial culture and the algal biomass; and
 c. fermenting the algal biomass under conditions and for a period of time sufficient to produce lactic acid, a salt or an ester thereof; and
 d. isolating said lactic acid, a salt or an ester thereof,
wherein the microbial culture comprises a thermophilic microorganism capable of surviving that survives in high temperature conditions above 70° C., and wherein the thermophilic microorganism is a microorganism of from the genus *Caldicellulosiruptor* or of the genus *Thermoanaerobacter*, and wherein the *Caldicellulosiruptor* is an isolated strain selected from the group consisting of *Caldicellulosiruptor* sp DIB041C, deposited as DSM 25771, *Caldicellulosiruptor* sp DIB087C, deposited as DSM 25772, *Caldicellulosiruptor* sp DIB103C, deposited as DSM 25773, *Caldicellulosiruptor* sp DIB104C, deposited as DSM 25774 *Caldicellulosiruptor* sp DIB107C, deposited as DSM 25775, and microorganisms obtained from, progenies or homologs thereof.

2. The method according to claim 1, wherein the thermophilic microorganism is from the species *Caldicellulosiruptor saccharolyticus*.

3. The method according to claim 1, wherein the thermophilic microorganism is an isolated strain of the genus *Thermoanaerobacter*, and wherein the strain is selected from the group consisting of *Thermoanaerobacter* sp DIB087G, deposited as DSM 25777, *Thermoanaerobacter* sp, DIB103X, deposited as DSM 25776, *Thermoanaerobacter* sp, DIB104X, deposited as DSM 25778, *Thermoanaerobacter* sp DIB107X, deposited as DSM 25779, and microorganisms obtained from progenies or homologs thereof.

4. The method according to claim 1, wherein the period of time is 10 h to 300 h, 50 h to 200 h, or 80 h to 160 h, wherein the conditions comprises a temperature in the range between 55° C. and 80° C. or between 72° C. and 78° C., and wherein the conditions comprises a pH between 5 and 9 or between 6 and 8.

5. The method according to claim 1, wherein said algal biomass material is subjected to mechanical, thermochemical, and/or biochemical pretreatment.

6. The method according to claim 1, wherein the algal biomass material is treated with cellulose and hemicellulose degrading enzymes.

7. The method according to claim 1, wherein the algae are green algae from the class Chorophycea of the order Chlamydomonadales of the family Haematococcaceae of the genus *Haematococcus* and of the species *Haematococcus pluvialis* or *Nannochloropsis salina*.

8. The method according to claim 1, wherein the algal biomass material comprises intact algal cells.

* * * * *